(12) United States Patent
Yadav et al.

(10) Patent No.: US 8,754,243 B2
(45) Date of Patent: Jun. 17, 2014

(54) PROCESS FOR THE PREPARATION OF 1, 2, 4-TRIOXOLANE ANTIMALARIALS

(75) Inventors: Gyan Chand Yadav, Ghaziabad (IN); Harish N. Dorwal, Gurgaon (IN); Pooja Tanwar, New Delhi (IN); Udai Bhan Singh Gahlot, Udaipur (IN)

(73) Assignee: Ranbaxy Laboratories Limited, New Delhi (IN)

(*) Notice: Subject to any disclaimer, the term of this patent is extended or adjusted under 35 U.S.C. 154(b) by 130 days.

(21) Appl. No.: 13/264,830

(22) PCT Filed: Apr. 15, 2010

(86) PCT No.: PCT/IB2010/051656
§ 371 (c)(1),
(2), (4) Date: Mar. 30, 2012

(87) PCT Pub. No.: WO2010/119425
PCT Pub. Date: Oct. 21, 2010

(65) Prior Publication Data
US 2012/0178944 A1    Jul. 12, 2012

(30) Foreign Application Priority Data
Apr. 17, 2009   (IN) .............................. 798/DEL/2009

(51) Int. Cl.
*C07D 319/00*   (2006.01)

(52) U.S. Cl.
USPC .......................................... 549/340; 549/341

(58) Field of Classification Search
USPC ................................................ 549/340, 341
See application file for complete search history.

(56) References Cited

U.S. PATENT DOCUMENTS

| 6,906,205 B2 | 6/2005 | Vennerstrom et al. | ....... 549/341 |
| 2004/0039008 A1 | 2/2004 | Vennerstrom et al. | ....... 514/278 |

FOREIGN PATENT DOCUMENTS

WO   WO 2007/138435   12/2007   ........... C07D 323/02

OTHER PUBLICATIONS

Dong and Vennerstrom, "Peroxidic Antimalarials", *Expert Opinion on Therapeutic Patents*, 11(11):1753-1760 (2001).
Meshnick et al., "Artemisinin and the Antimalarial Endoperoxides: from Herbal Remedy to Targeted Chemotherapy", *Microbiological Reviews*, 60(2):301-315 (1996).
Vroman et al., "Current Progress in the Chemistry, Medicinal Chemistry and Drug Design of Artemisinin Based Antimalarials", *Current Pharmaceutical Design*, 5(2):101-138 (1999).
Dhingra et al., "Current status of artemisinin and its derivatives as antimalarial drugs", *Life Sciences*, 66(4):279-300 (1999).
Jefford, 1997. Peroxidic Antimalarials. In: Meyer and Testa, eds. *Advances in Drug Research*. vol. 29. USA: Academic Press Limited, 271-325.
Wesche et al., "Neurotoxicity of Artemisinin Analogs In Vitro", *Antimicrobial Agents and Chemotherapy*, 38(8):1813-1819 (1994).
White, "Clinical pharmacokinetics and pharmacodynamics of artemisinin and derivatives", *Transactions of the Royal Society of Tropical Medicine and Hygiene*, 88(Suppl. 1):41-43 (1994).
van Agtmael et al., "Artemisinin drugs in the treatment of malaria: from medicinal herb to registered medication" *Trends in Pharmacological Sciences*, 20(5):199-205 (1999).
Cumming, Ploypradith, and Posner, 1997. Antimalarial Activity of Artemisinin (Qinghaosu) and Related Trioxanes: Mechanism(s) of Action. In: August, Anders, Murad, and Coyle, eds. *Advances in Pharmacology*. vol. 37. USA: Academic Press, Inc., 253-297.
Dong et al., "Effect of functional group polarity on the antimalarial activity of spiro and dispiro-1,2,4-trioxolanes", *Bioorganic & Medicinal Chemistry*, 14(18):6368-6382 (2006).

*Primary Examiner* — Andrew D Kosar
*Assistant Examiner* — Raymond Covington

(57) ABSTRACT

This invention relates to an improved process for the preparation of compounds of Formula I, salts of the free base cis-adamantane-2-spiro-3'-8'-[[[(2'-amino-2'-methylpropyl)amino]carbonyl]methyl]-1',2',4'-trioxaspiro[4.5]decane, Formula (I) wherein X is an anion. The compounds of Formula (I) have antimalarial activity.

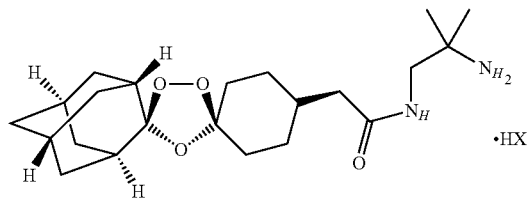

Formula I

11 Claims, No Drawings

PROCESS FOR THE PREPARATION OF 1, 2, 4-TRIOXOLANE ANTIMALARIALS

FIELD OF THE INVENTION

This invention relates to an improved process for the preparation of compounds of Formula I, salts of the free base cis-adamantane-2-spiro-3'-8'-[[[(2'-amino-2'-methylpropyl)amino]carbonyl]methyl]-1',2',4'-trioxaspiro[4.5]decane,

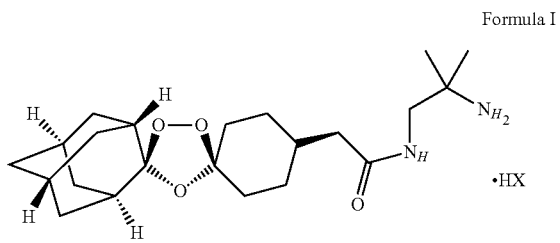

Formula I wherein X is an anion. The compounds of Formula I have antimalarial activity.

BACKGROUND OF THE INVENTION

Malaria is an acute and often chronic infectious disease resulting from the presence of protozoan parasites within red blood cells. Caused by single-celled parasites of the genus *Plasmodium*, malaria is transmitted from person to person by the bite of female mosquitoes.

The discovery of artemisinin (qinghaosu), a naturally occurring endoperoxide sesquiterpene lactone, triggered substantial efforts to elucidate its molecular mechanism of action and to identify novel antimalarial peroxides (Dong and Vennerstrom, *Expert Opin. Ther. Patents* 11, 1753-1760, (2001)). Many synthetic 1,2,4-trioxanes, 1,2,4,5-tetraoxanes, and other endoperoxides have been prepared.

A synthetic procedure for preparing compounds of Formula I, salts of the free base cis-adamantane-2-spiro-3'-8'-[[[(2'-amino-2'-methylpropyl)amino]carbonyl]methyl]-1',2',4'-trioxaspiro[4.5]decane has been disclosed in U.S. Pat. No. 6,906,205. WO 2007138435 also discloses a synthetic procedure for preparing compounds of Formula I. The free base obtained by this procedure involves the formation of dimer impurity, which affects the purity of the free base.

Therefore, there is a need to develop a process which provides the free base of high purity.

SUMMARY OF THE INVENTION

In one aspect, the present invention provides an improved, economically attractive and an easily operable process, which results in reduced solvent usage.

In another aspect, the present invention provides an improved process for the preparation of compounds of Formula I, salts of the free base cis-adamantane-2-spiro-3'-8'-[[[(2'-amino-2'-methylpropyl)amino]carbonyl]methyl]-1',2', 4'-trioxaspiro[4.5]decane,

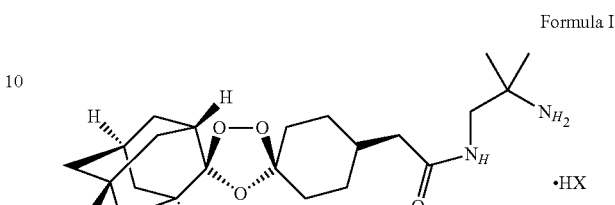

Formula I in high yield, wherein X is an anion, for example, acetate, adipate, alginate, citrate, aspartate, benzoate, benzene sulfonate, bisulfate, butyrate, camphorate, camphor sulfonate, digluconate, glycerophosphate, glycolate, malonate, hemisulfate, heptanoate, hexanoate, fumarate, hydrochloride, hydrobromide, hydroiodide, isethionate, lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate or undecanoate, wherein the freebase which is used has high purity.

In another aspect, the present invention provides an improved process for the preparation of free base, cis-adamantane-2-spiro-3'-8'-[[[(2'-amino-2'-methylpropyl)amino]carbonyl]methyl]-1',2',4'-trioxaspiro[4.5]decane, of Formula III, having high purity.

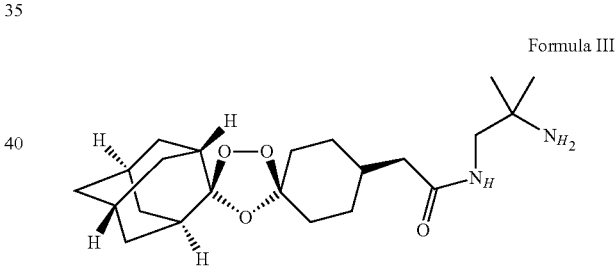

Formula III

The term "high purity" refers to purity (HPLC) not less than 96%.

In another aspect, the present invention provides an improved process for the preparation of free base, cis-adamantane-2-spiro-3'-8'-[[[(2'-amino-2'-methylpropyl)amino]carbonyl]methyl]-1',2',4'-trioxaspiro[4.5]decane, having no dimer impurity of Formula IV.

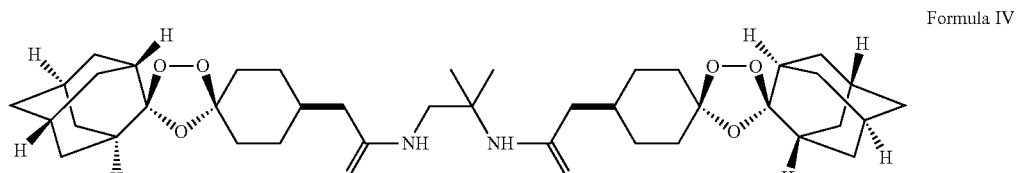

Formula IV

DETAILED DESCRIPTION OF THE INVENTION

The process for the preparation of free base, cis-adamantane-2-spiro-3'-8'[[[(2'-amino-2'-methylpropyl)amino]carbonyl]methyl]-1',2',4'-trioxaspiro[4.5]decane, comprises the reaction of the compound of Formula II

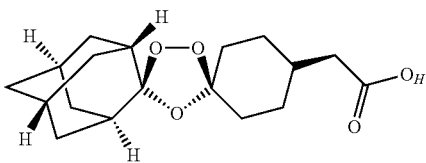

Formula II with an activating agent, for example, methyl chloroformate, ethyl chloroformate, propyl chloroformate, n-butyl chloroformate, isobutyl chloroformate or pivaloyl chloride leading to the formation of mixed anhydride, which is either reacted in situ reaction with 1,2-diamino-2-methylpropane, or mixed anhydride is isolated and is reacted with 1,2-diamino-2-methylpropane, to give free base of Formula III.

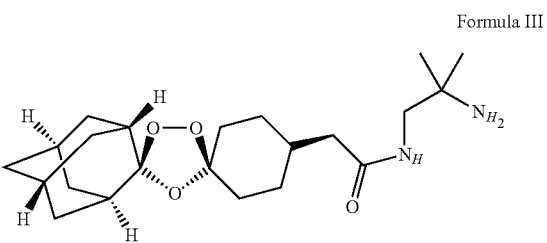

Formula III

With an objective of avoiding the formation of dimer impurity during the formation of free base, different reaction conditions including various combinations of solvents or different volumes of solvents and/or different amounts of 1,2-diamino-2-methylpropane were used.

When 1.8-3 mole equivalents of 1,2-diamino-2-methylpropane were used in 20-80 times w/v of dual solvent system of dichloromethane and ethanol (in the ratio of 1:1 v/v), free base having no dimer impurity was obtained.

The reaction of a compound of Formula II with an activating agent and 1,2-diamino-2-methylpropane can be carried out in the presence of an organic base, for example, trimethyl amine, triethyl amine, isopropyl amine or mixture(s) thereof.

The compound of Formula III on reaction with an acid of Formula HX (wherein X can be the same as defined earlier) gives compounds of Formula I.

The reaction of a compound of Formula III with an acid of Formula HX to give a compound of Formula I can be carried out in a solvent, for example, an alcoholic solvent, for example, methanol, ethanol or isopropanol, hydrocarbon solvent, for example, hexane or heptane or mixture(s) thereof.

Compound of Formula II can be prepared by following the procedures given in WO2007138435.

While the present invention has been described in terms of its specific embodiments, certain modifications and equivalents will be apparent to those skilled in the art and are included within the scope of the present invention. The examples are provided to illustrate particular aspects of the disclosure and do not limit the scope of the invention.

EXAMPLES

Example 1

Preparation of (1s,4s)-dispiro[cyclohexane-1,3'-[1,2,4]trioxolane-5',2"-tricyclo[3.3.1.1$^{3,7}$]decan]-4-ylacetic acid The title compound was prepared by following the procedure given in WO 07138435.

Example 2(a)

Preparation of cis-adamantane-2-spiro-3'-8'-[[[(2'-amino-2'-methylpropyl)amino]carbonyl]methyl]-1',2',4'-trioxaspiro[4.5]decane (1s,4s)-dispiro[cyclohexane-1,3'-[1,2,4]trioxolane-5',2"-tricyclo[3.3.1.1$^{3,7}$]decan]-4-ylacetic acid (10 gm, 31 mmol, 1 equiv) (example 1) was taken in dichloromethane (100 ml) at room temperature under dry nitrogen atmosphere. Tri ethylamine (6.9 ml, 49.6 mmol, 1.6 equiv) was added at room temperature. The reaction mixture was cooled to −10° C. Ethyl chloroformate (3.36 gm, 31 mmol, 1 equiv) was added slowly at −10 to −5° C., under stirring. The mixture was stirred for about 20-30 minutes. The resulting mixed anhydride reaction mixture was added dropwise at −10 to −5° C. to a previously prepared solution of 1,2-diamino-2-methylpropane (this solution was prepared by adding 1,2-diamino-2-methylpropane (5.47 gm, 62 mmol, 2 equiv) to ethanol (100 ml) at room temperature and it was cooled to −10° C.). The temperature of reaction mixture was raised to room temperature. The organic layer was concentrated at 35 to 40° C. under reduced pressure to get a thick oily mass. Dichloromethane (200 ml) was added at room temperature under stirring. Deionized (DI) water (100 ml) was added at room temperature under stirring. The reaction mixture was stirred at room temperature for about 30 minutes and settled for about 30 minutes at room temperature. The organic layer was separated. It was washed with 100 ml of saturated sodium bicarbonate solution. The layer was settled for about 30 minutes and the organic layer was separated. The organic layer was washed with 50 ml of DI water at room temperature. The layer was settled for about 30 minutes and the organic layer was separated. The organic layer was concentrated at 35 to 40° C. under reduced pressure. Hexane (100 ml) was added and the reaction mass was stirred at 35 to 40° C. for about 30 minutes and cooled to room temperature. The solid was filtered and washed with hexane (10 ml). The material obtained was dried at room temperature under reduced pressure for about 3 h till constant weight was obtained.

Yield: 11.3 gm (1.13 w/w), 92.81%
Mass 393, HPLC Purity 97.86%,
$^1$HNMR (400 MHz, DMSO-d$_6$): δ 0.92 (s, 6H), 1.10-1.07 (m, 2H), 1.89-1.64 (m, 21H), 2.03-2.01 (d, 2H), 2.93 (d, 2H).

Example 2(b)

Preparation of cis-adamantane-2-spiro-3'-8'-[[[(2'-amino-2'-methylpropyl)amino]carbonyl]methyl]-1',2',4'-trioxaspiro[4.5]decane (1s,4s)-dispiro[cyclohexane-1,3'-[1,2,4]trioxolane-5',2"-tricyclo[3.3.1.1$^{3,7}$]decan]-4-ylacetic acid (15 gm, 46 mmol, 1 equiv) (example 1) was taken in dichloromethane (150 ml) at room temperature under dry nitrogen atmosphere. Tri ethylamine (13.0 ml, 93 mmol, 2.0 equiv) was added at room temperature. The reaction mixture was cooled to −10° C. Ethyl chloroformate (5.55 gm, 51 mmol, 1.1 equiv) was added slowly at −10 to −5° C., under stirring. The mixture was stirred for about 30-45 minutes. The resulting mixed anhydride reaction mixture was added dropwise at −10 to −5° C. to a previously prepared solution of 1,2-diamino-2-methylpropane (this solution was prepared by adding 1,2-diamino-2-methylpropane (8.2 gm, 93 mmol, 2 equiv) to ethanol (150 ml) at room temperature and it was cooled to −10° C.). The vessel was washed with dichloromethane-ethanol solution (7.5+7.5 ml). The temperature of reaction mixture was raised to room temperature. The organic layer was concentrated at 35 to 40° C. under reduced pressure to get a thick oily mass. Dichloromethane (300 ml) was added at room temperature under stirring. Deionized (DI) water (150 ml) was added at room temperature under stirring. The reaction mixture was stirred at room temperature for about 30 minutes and settled for about 30 minutes at room temperature. The organic layer was separated. It was washed with 150 ml of saturated sodium bicarbonate solution. The layer was settled for about 30 minutes and the organic layer was separated. The organic layer was washed with 150 ml of DI water at room temperature. The layer was settled for about 30 minutes and the organic layer was separated. The organic layer was concentrated at 35 to 40° C. under reduced pressure. Hexane (150 ml) was added and the reaction mass was stirred at 35 to 40° C. for about 30 minutes and cooled to room temperature. The solid was filtered and washed with hexane (15 ml). The material obtained was dried at room temperature under reduced pressure for 10-12 hrs till constant weight was obtained.

Yield: 16.8 gm (1.12 w/w), 92.0%
Mass 393, HPLC Purity 96.72%,
$^1$HNMR (400 MHz, DMSO-$d_6$): δ 0.93 (s, 6H), 1.10-1.05 (m, 2H), 1.89-1.64 (m, 21H), 2.03-2.01 (d, 2H), 2.93 (d, 2H).

Example 3

Preparation of cis-adamantane-2-spiro-3'-8'-[[[(2'-amino-2'-methylpropyl)amino]carbonyl]methyl]-1',2',4'-trioxaspiro[4.5]decane Step a: Preparation of (1s,4s)-dispiro[cyclohexane-1,3'-[1,2,4]trioxolane-5',2"-tricyclo[3.3.1.1$^{3,7}$]decan]-4-ylacetyl ethyl carbonate (1s,4s)-Dispiro[cyclohexane-1,3'-[1,2,4]trioxolane-5',2"-tricyclo[3.3.1.1$^{3,7}$]decan]-4-ylacetic acid (1.5 gm, 4.65 mmol, 1 equiv) was taken in dichloromethane (15 ml) at room temperature under dry nitrogen atmosphere. Tri ethylamine (0.75 gm, 7.44 mmol, 1.6 equiv) was added at room temperature. The reaction mixture was cooled to −10° C. Ethyl chloroformate (0.50 gm, 4.65 mmol, 1 equiv) was added slowly at −10 to −5° C., under stirring. The mixture was stirred for about 20-30 minutes. The reaction mass was diluted with dichloromethane (20 ml) and deionized water (15 ml) was added at room temperature under stirring. The reaction mixture was stirred at room temperature for about 10 minutes and settled for about 15 minutes at room temperature. The organic layer was separated. It was washed with 10 ml of 25% sodium chloride solution. The layer was settled for about 15 minutes and the organic layer was separated. It was concentrated at 25 to 30° C. under reduced pressure to obtain solid residue. It was further dried at 30-35° C. under reduced pressure for about 3 h till constant weight was obtained.

Yield: 1.70 gm (1.13 w/w), 92.63%
Mass 394.45, Mass Purity: 99.58%
$^1$HNMR (400 MHz, DMSO-$d_6$): δ 0.857 (s, 6H), 1.04-1.01 (m, 2H), 1.82-1.57 (m, 21H), 1.96-1.95 (d, 2H), 2.86-2.85 (d, 2H).

Step b: Preparation of cis-adamantane-2-spiro-3'-8'-[[[(2'-amino-2'-methylpropyl)amino]carbonyl]methyl]-1',2',4'-trioxaspiro[4.5]decane 1,2-Diamino-2-methylpropane (0.45 gm, 5.10 mmol, 2 equiv) was taken in ethanol (10 ml) at room temperature under dry nitrogen atmosphere. The reaction mixture was cooled to −10° C. Mixed anhydride solution [this solution was prepared by adding (1s,4s)-dispiro [cyclohexane-1,3'-[1,2,4]trioxolane-5',2"-tricyclo[3.3.1.1$^{3,7}$]decan]-4-ylacetyl ethyl carbonate (1.0 gm, 2.53 mmol, 1 equiv) (step a) to dichloromethane (10 ml) at room temperature] was added drop wise at −10 to −5° C., under stirring. The temperature of reaction mixture was raised to room temperature. The organic layer was concentrated at 35 to 40° C. under reduced pressure to get a thick oily mass. Dichloromethane (20 ml) was added at room temperature under stirring. Deionized water (10 ml) was added at room temperature under stirring. The reaction mixture was stirred at room temperature for about 30 minutes and settled for about 30 minutes at room temperature. The organic layer was separated. It was washed with 10 ml of saturated sodium bicarbonate solution. The layer was settled for about 30 minutes and the organic layer was separated. The organic layer was washed with 5 ml of DI water at room temperature. The layer was settled for about 30 minutes and the organic layer was separated. The organic layer was concentrated at 35 to 40° C. under reduced pressure. Hexane (10 ml) was added and the reaction mass was stirred at 35 to 40° C. for about 30 minutes and cooled to room temperature. The solid was filtered and washed with hexane (1.0 ml). The material obtained was dried at room temperature under reduced pressure for about 3 hrs till constant weight was obtained.

Yield: 0.9 gm (0.9 w/w), 90.44%
Mass 393, HPLC Purity: 98.83%,
$^1$HNMR (400 MHz, DMSO-$d_6$): δ 0.855 (s, 6H), 1.03-1.00 (m, 2H), 1.82-1.57 (m, 21H), 1.96-1.94 (d, 2H), 2.86-2.85 (d, 2H).

Example 4

Preparation of cis-adamantane-2-spiro-3'-8'-[[[(2'-amino-2'-methylpropyl)amino]carbonyl]methyl]-1',2',4'-trioxaspiro[4.5]decane maleate To a solution of cis-adamantane-2-spiro-3'-8'-[[[(2'-amino-2'-methylpropyl)amino]carbonyl]methyl]-1',2',4'-trioxaspiro[4.5]decane (10 gm, 25.47 mmole, 1 equiv) (example 2 (a), 2 (b) or 3) in ethanol (25 ml) was added a solution of maleic acid (2.89 gm, 24.96 mmole, 0.98 equiv) in ethanol (15 ml) and the reaction mixture was stirred for about 1 h. To this clear solution, n-hexane (120 ml) was added at room temperature in about 1 h and then reaction mixture was stirred for about 4 to 5 h. It was then cooled to 5 to 10° C. and stirred for about another 1 h and filtered at the same temperature. The cake was slurry washed with n-hexane (10 ml) and dried under vacuum at 25-35° C. for about 12 to 16 hrs.

Yield: 10.99 gm, 85.19%, mp: 149° C. (decomp), (M$^+$+1) 393.5,
$^1$HNMR (400 MHz, DMSO-$d_6$): δ 1.05-1.11 (m, 2H), 1.16 (s, 6H), 1.64-1.89 (m, 21H), 2.07 (d, 2H), 3.20 (d, 2H), 6.02 (d, 2H), 7.7 (bs, 2H), 8.07 (t, 1H).

We claim:
1. A process for the preparation of cis-adamantane-2-spiro-3'-8'-[[[(2'-amino-2'-methylpropyl)amino]carbonyl]methyl]-1',2',4'-trioxaspiro[4.5]decane, of Formula III

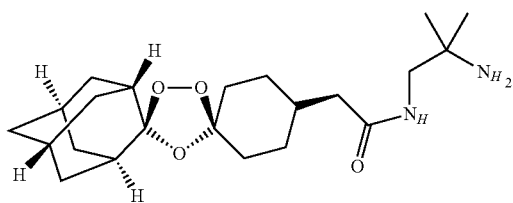

Formula III having no dimer impurity of Formula IV,

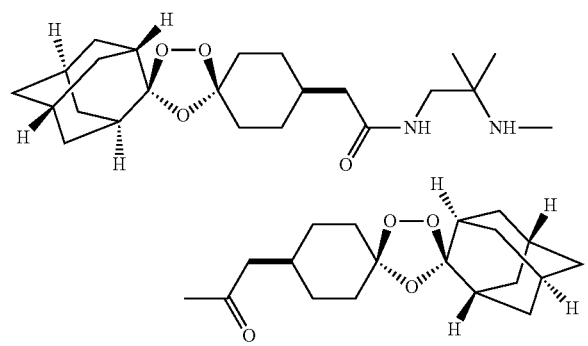

Formula IV wherein the process comprises,
(a) reacting a compound of Formula II

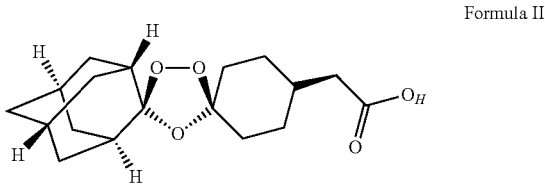

Formula II in dichloromethane with an activating agent forming a mixed anhydride, and
(b) reacting the mixed anhydride in situ with an ethanolic solution of 1,2-diamino-2-methylpropane to give a compound of Formula III, wherein 1.8-3 mole equivalents of 1,2-diamino-2-methylpropane are used in 20-80 times w/v of solvent system of dichloromethane and ethanol (in the ratio of 1:1 v/v).

2. A process for the preparation of cis-adamantane-2-spiro-3'-8'-[[[(2'-amino-2'-methylpropyl)amino]carbonyl]methyl]-1',2',4'-trioxaspiro[4.5]decane, of Formula III

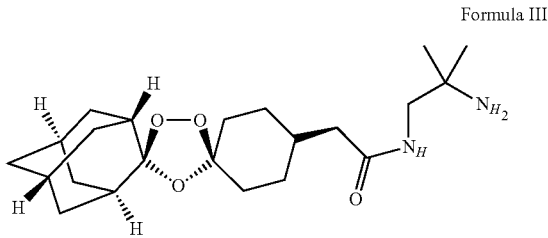

Formula III wherein the process comprises,
(a) reacting a compound of Formula II

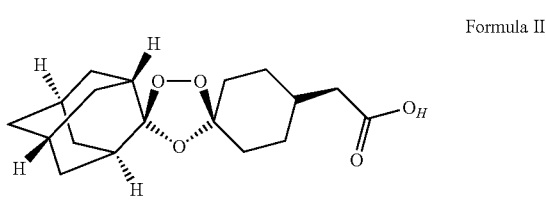

Formula II in dichloromethane with an activating agent forming a mixed anhydride,
(b) isolating the mixed anhydride, and
(c) reacting the dichloromethane solution of mixed anhydride with an ethanolic solution of 1,2-diamino-2-methylpropane, to give a compound of Formula III, wherein 1.8-3 mole equivalents of 1,2-diamino-2-methylpropane are used in 20-80 times w/v of solvent system of dichloromethane and ethanol (in the ratio of 1:1 v/v).

3. The process of claim 1 or 2 wherein the activating agent is selected from methyl chloroformate, ethyl chloroformate, propyl chloroformate, n-butyl chloroformate, isobutyl chloroformate and pivaloyl chloride.

4. The process of claim 1 or 2 wherein the reaction of the compound of Formula II with the activating agent and 1,2-diamino-2-methylpropane to give the compound of Formula III is carried out in the presence of an organic base.

5. The process of claim 4 wherein the organic base is trimethyl amine, triethyl amine, isopropyl amine or mixture(s) thereof.

6. The process of claim 1 or 2 wherein cis-adamantane-2-spiro-3'-8'-[[[(2'-amino-2'-methylpropyl)amino]carbonyl]methyl]-1',2',4'-trioxaspiro[4.5]decane of Formula III has HPLC purity not less than 96%.

7. The process of claim 1 or 2, which further comprises the conversion of the produced cis-adamantane-2-spiro-3'-8'-[[[(2'-amino-2'-methylpropyl)amino]carbonyl]methyl]-1',2', 4'-trioxaspiro[4.5]decane, of Formula III

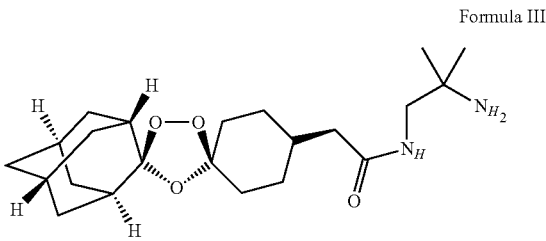

Formula III having no dimer impurity of Formula IV,

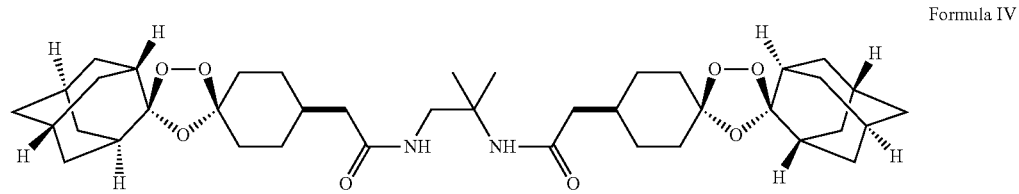

Formula IV having no dimer impurity of Formula IV,

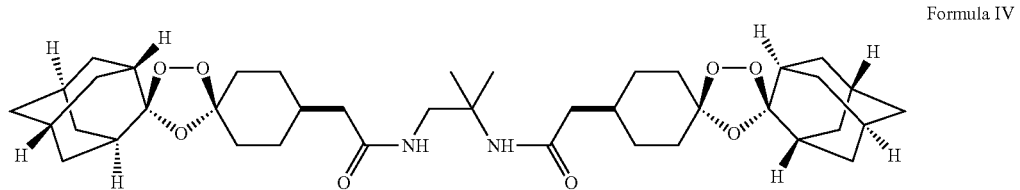

Formula IV to compounds of Formula I,

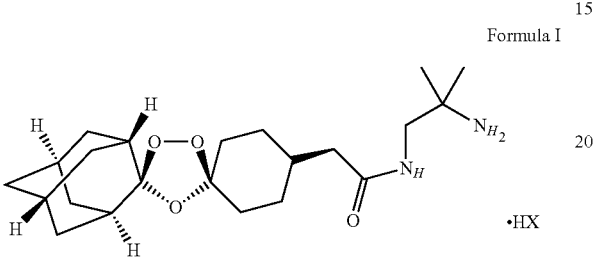

Formula I wherein the process comprises reacting the compound of Formula III with an acid of Formula HX to give the compounds of Formula I, wherein X is an anion selected from acetate, adipate, alginate, citrate, aspartate, benzoate, benzene sulfonate, bisulfate, butyrate, camphorate, camphor sulfonate, digluconate, glycerophosphate, glycolate, malonate, hemisulfate, heptanoate, hexanoate, fumarate, hydrochloride, hydrobromide, hydroiodide, isethionate, lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate or undecanoate.

8. The process of claim 7 wherein cis-adamantane-2-spiro-3'-8'-[[[(2'-amino-2'-methylpropyl)amino]carbonyl]methyl]-1',2',4'-trioxaspiro[4.5]decane of Formula III has HPLC purity not less than 96%.

9. The process of claim 7 wherein the reaction of the compound of Formula III with the acid of Formula HX to give the compound of Formula I is carried out in an alcoholic solvent, hydrocarbon solvent or mixture(s) thereof.

10. The process of claim 9 wherein the alcoholic solvent is methanol, ethanol, isopropanol or mixture(s) thereof.

11. The process of claim 9 wherein the hydrocarbon solvent is hexane, heptane or mixture(s) thereof.

* * * * *